United States Patent [19]

Burhop et al.

[11] Patent Number: 5,733,869
[45] Date of Patent: Mar. 31, 1998

[54] THERAPEUTIC ADMINISTRATION OF HEMOGLOBIN IN CARDIAC ARREST

[75] Inventors: Kenneth E. Burhop, Mundelein, Ill.; Moses S. S. Chow, South Glastonbury, Conn.

[73] Assignee: Baxter International, Inc., Deerfield, Ill.

[21] Appl. No.: 540,115

[22] Filed: Oct. 6, 1995

[51] Int. Cl.$^6$ .............................. A61K 38/42; A61N 1/39
[52] U.S. Cl. ............................. 514/6; 604/50; 604/52; 607/3
[58] Field of Search ............... 436/66, 67; 514/6; 530/385; 607/3, 5, 6, 4, 7, 8; 604/50, 51, 52, 53

[56] References Cited

U.S. PATENT DOCUMENTS

| | | | |
|---|---|---|---|
| Re. 34,271 | 6/1993 | Walder | 530/385 |
| 4,053,590 | 10/1977 | Bonsen et al. | 514/6 |
| 4,061,736 | 12/1977 | Morris et al. | 514/6 |
| 4,336,248 | 6/1982 | Bonhard et al. | 530/354 |
| 4,529,719 | 7/1985 | Tye | 514/6 |
| 4,598,064 | 7/1986 | Walder | 514/6 |
| 4,600,531 | 7/1986 | Walder | 530/385 |
| 4,757,052 | 7/1988 | Markov | 514/23 |
| 4,826,811 | 5/1989 | Sehgal et al. | 514/6 |
| 4,866,096 | 9/1989 | Schweighardt | 514/756 |
| 4,873,230 | 10/1989 | Belzer et al. | 514/60 |
| 4,988,515 | 1/1991 | Buckberg | 424/529 |
| 4,994,444 | 2/1991 | Zikria | 514/60 |
| 5,084,558 | 1/1992 | Rausch et al. | 530/385 |
| 5,194,590 | 3/1993 | Sehgal et al. | 530/385 |
| 5,248,785 | 9/1993 | Abraham et al. | 548/416 |
| 5,268,500 | 12/1993 | Lalezari et al. | 560/34 |
| 5,296,465 | 3/1994 | Rausch et al. | 514/6 |
| 5,306,508 | 4/1994 | Kossovsky et al. | 424/493 |
| 5,334,706 | 8/1994 | Przybelski | 530/385 |
| 5,370,870 | 12/1994 | Wong | 424/85.1 |
| 5,386,014 | 1/1995 | Nho et al. | 530/385 |
| 5,413,558 | 5/1995 | Paradis | 604/101 |
| 5,428,007 | 6/1995 | Fischer et al. | 514/6 |
| 5,432,191 | 7/1995 | Abraham et al. | 514/421 |
| 5,464,814 | 11/1995 | Sehgal et al. | 514/6 |
| 5,510,464 | 4/1996 | Przybelski | 530/385 |

FOREIGN PATENT DOCUMENTS

| | | |
|---|---|---|
| 622610 | 4/1992 | Australia . |
| 1312009 | 12/1992 | Canada . |
| 2074852 | 1/1994 | Canada . |
| 0140640 | 5/1985 | European Pat. Off. . |
| 0361719 | 4/1990 | European Pat. Off. . |
| 0361720 | 4/1990 | European Pat. Off. . |
| 0446699 | 9/1991 | European Pat. Off. . |
| 0277289 | 4/1992 | European Pat. Off. . |
| 2551660 | 3/1985 | France . |
| 2640141 | 6/1990 | France . |
| 8404248 | 11/1984 | WIPO . |
| 8707832 | 12/1987 | WIPO . |
| 8803408 | 5/1988 | WIPO . |
| 9316720 | 9/1993 | WIPO . |

OTHER PUBLICATIONS

Emergency Cardiac Care Committee and Subcommitess, American Heart Assoc. Guidelines for Cardiopulmonary Resuscitation and Emergency Cardiac Care, II: Adult Basic Life Support. JAMA. 1992. vol. 268, pp. 2184–2198.

Cole et al, Effect of Oncotic Pressure of Diaspirin Cross–Linked . . . Anesth. Analg. vol. 83, pp. 342–347, 1996.

(List continued on next page.)

*Primary Examiner*—Jeffrey E. Russel
*Attorney, Agent, or Firm*—Senniger, Powers, Leaviit & Roedel

[57] ABSTRACT

Administration of stroma-free crosslinked hemoglobin during standard cardiac pulmonary resuscitation procedures enhances return of spontaneous circulation following electrical defibrillation. The difficulty in restoring spontaneous circulation directly correlates with a generally poor prognosis in cases of cardiac arrest. The therapeutic effect of hemoglobin as an adjunct to conventional treatment may thereby improve survival.

11 Claims, 1 Drawing Sheet

OTHER PUBLICATIONS

Linz et al, Diaspirin Crosslinked Hemoglobin Infusion . . . FASEB J. vol. 9, No. 3, p. A9, Abstract No. 54, 1995.

Cocks et al, Oxyhaemoglobin Increases The Production of . . . Eur. J. Pharmac. vol. 196, pp. 177–182, 1991.

Riess, Fluorocarbon–Based in Vivo Oxygen Transport . . . Vox Sang. vol. 61, pp. 225–239, 1991.

Rosenkranz et al, Warm Induction of Carioplegia With . . . J. Thorac. Cardiovasc. Surg. vol. 86, pp. 507–518, 1983.

Amberson et al., Clinical Experience with Hemoglobin–Saline Solutions, Physiology, vol. 1, No. 7, pp. 469–489, 1949.

Amberson et al., On the Use of Ringer Locke Solutions Containing Hemoglobin as a Substitute for Normal Blood in Mammals, Journal of Cellular and Comparative Physiology, vol. 5, pp. 359–382, 1934.

American Heart Association, Advanced Cardiac Life Support Algorithms and Drugs: A 1993 Handbook for Adult and Pediatric Providers, JAMA, vol. 268, pp. 2199–2241, 1992.

Biro et al., Coronary Vascular Actions of Stroma–Free Hemoglobin Preparations, Artificial Organs, vol. 12, No. 1, pp. 40–50, 1988.

Biro et al., The Effect of Hemodilution with Stroma–Free Hemoglobin and Dextran on Collateral Perfusion of Ischemic Myocardium in the Dog, American Heart Journal, vol. 99, No. 1, pp. 64–75, 1980.

Bleske et al., Effects of Different Dosages and Modes of Sodium Bicarbonate Administration During Cardiopulmonary Resuscitation, American Journal of Emergency Medicine, vol. 10, No. 6, pp. 525–532, 1992.

Block et al., Morphology After Transluminal Angioplasty in Human Beings, The New England Journal of Medicine, vol. 305, No. 7, pp. 382–385, 1981.

Bowes et al., Diaspirin Cross–Linked Hemogolbin Improves Neurological Outcome Following Reversible but Not Irreversible CNS Ischemia in Rabbits, Chemical Abstracts, vol. 122, No. 13, Abstract No. 151066q, pp. 45–46, 1995.

Capparelli et al., Differences in Systematic and Myocardial Blood Acid–Base Status During Cardiopulmonary resuscitation, Critical Care Medicine, vol. 17, No. 5, pp. 442–446, 1989.

Capparelli et al., Diltiazem Improves Resuscitation from Experimental Ventricular Fibrillation in Dogs, Critical Care Medicine, vol. 20, No. 8, pp. 1140–1145, 1992.

Chow et al., Beneficial Effects of Diaspirin Cross–Linked Hemoglobin During Fibrillatory Arrest and CPR in an Animal Model, Circulation, vol. 92, No. 8, p. 833, 1995.

Chow et al., Effect of Exernal Cardiopulmonary Resuscitation on Lidocaine Pharmacokinetics in Dogs, The Journal of Pharmacology and Experimental Therapeutics, vol. 224, No. 3, pp. 531–537, 1983.

Coetzee et al., Halothane and the Reperfusion Injury in the Intact Animal Model, Anesth. Analg., vol. 76, No. 4, pp. 734–744, 1993.

Cole et al., Focal Cerebral Ischemia in Rats: Effect of Hemodilution with x–x Cross–Linked Hemoglobin on CBF, Journal of Cerebral Blood Flow & Metabolism, vol. 12, No. 6, pp. 971–976, 1992.

Cole et al., Focal Cerebral Ischemia in Rats: Effect of Hemodilution with x–x Cross–Linked Hemoglobin on Brain Injury and Edema, The Canadian Journal of Neurological Sciences, vol. 20, No. 1, pp. 30–36, 1993.

Cole et al., Focal Cerebral Ischemia in Rats: Effect of Hypervolemic Hemodilution with Diaspirin Cross–Linked Hemoglobin Versus Albumin on Brain Injury and Edema, Anesthesiology, vol. 78, No. 2, pp. 335–342, 1993.

Cole et al., Focal Cerebral Ischemia: Effects of Oncotic Pressure of a Molecular Hemoglobin Preparation on Infarct Volume in Rats, Anesth. Analog, vol. 80, No. S82, 1995.

Cole et al., Hemodilution during Cerebral Ischemia in Rats: Effects of Stroma–Free Hemoglobin on Brain Injury, Anseth. Analog, vol. 74, Abstract S50, 1992.

Cole et al., The Effect of Molecular Hemoglobin's Nitric Oxide Binding Properties, Anesth. Analog, vol. 80, No. S83, 1995.

Elger et al., Magnetic Resonance Imaging Study on the Effect of Levemopamil on the Size of Intracerebral Hemorrhage in Rats, Stroke, vol. 25, No. 9, pp. 1836–1841, 1994.

Estep, Efficacy and Safety of a Diaspirin Modified Hemoglobin Solution, ISBT Presentation, 1988.

Feola et al., Improved Oxygenation of Ischemic Myocardium by Hemodilution with Stroma–Free Hemoglobin Solution, Chest, vol. 75, No. 3, pp. 369–375, 1979.

Foley et al., Cytotoxic Effects of Bloody Cerebrospinal Fluid on Cerebral Endothelial Cells in Culture, Journal of Neurosurgery, vol. 81, pp. 87–92, 1994.

Forster et al., The Use of Stroma–Free Hemoglobin Solutions as Blood Substitute, Infusionsther Klin Ernahr., vol. 4, No. 2, pp. 122–126, (abstract), 1977.

Greenburg et al., Intravascular Persistence and Oxygen Delivery of Pyridoxalated, Stroma–Free Hemoglobin During Gradations of Hypotension, Surgery, vol. 86, No. 1, pp. 13–16, 1979 (abstract only).

Grotta, A Glimpse to the Future: Multitherapy Trials, Cerebrovasc. Dis., vol. 5, Suppl. 1, pp. 27–30, 1995.

Halstenson et al., Pharmacologic Profile of Diaspirin Cross–linked Hemoglobin (DCLHb) in Hemodialysis (HD) Patients, Journal of American Society of Nephrology, vol. 5, No. 3, Abstract 84P, pp. 451, 1994.

Hariman et al., Regional Changes in Blood Flow, Extracellular Potassium and Conduction During Myocardial Ischemia and Reperfusion, JACC, vol. 21, No. 1, pp. 798–808, 1993.

Hauck et al., Intracoronary Diaspirin Crosslinked Hemoglobin (DCLHb) Infusion During Coronary Balloon Occlusion in Dogs and Pigs, ABSTRACT–Biomaterials, Artificial Cells, and Immobilization Biotechnology, vol. 19, No. 2, 1991.

Jakobsen, Brain Ischemia In Subarachnoid Hemorrhage, pp. 3–32, 1992.

Jan et al., Coronary Hemodynamics and Oxygen Utilization After Hematocrit Variations in Hemorrhage, Am. J. Physiol., vol. 239, pp. H326–H332, 1980.

Jennings et al., Reperfusion Injury, Definitions and Historical Background, Myocardial Protection: the Pathophysiology of Reperfusion and Reperfusion Injury, pp. 1–11, 1992.

Jeroudi et al., Myocardial Reperfusion Injury: Role of Oxygen Radicals and Potential Therapy with Antioxidants, The American Journal of Cardiology, vol. 73, pp. 2B–7B, 1994.

Kim et al., Effects of Hemoglobin Perfusion of Contractile Function of the Isolated Ventricular Septa, Biomat. Art. Cells, Art. Org., vol. 16, Nos. 1–3, 331–345, 1988.

Kim et al., Effects of Hemoglobin Perfusion on Contractile Function of the Isolated Ventricular Septa, Chemical Abstracts, vol. 109, No. 21, Abstract No. 183, 274d, p. 38, 1988.

Kloner, Does Reperfusion Injury Exist in Humans?, J. Am. Coll. Cardiol., vol. 21, No. 2, pp. 537–545, 1993.

Lie et al., The Reasons Why Clinical Cardiologists Disregard Reperfusion Arrhythmias, Cardiovascular Research, vol. 27, p. 1906, 1993.

Liu et al., Reduction of Postischaemic Ventricular Dysfunction and Arrhythmias by Trapping Hydroxyl Radicals with Salicyclic Acid, Int. J. Tiss. Reac., vol. 15, No. 1, pp. 25–30, 1993.

Marks, Hemoglobin Solution Effects on the Heart, Letterman Army Institute of Research, Report No. 219, 1986.

Messmer et al., Oxygen Supply to the Tissues During Limited Normovolemic Hemodilution, Res. Exp. Med., vol. 159, pp. 152–166, 1973.

McKenzie et al., Effects of Diaspirin Crosslinked Hemoglobin During Coronary Angioplasty in the Swine, Cardiovascular Research, vol. 28, No. 8, pp. 1188–1192, 1994.

McKenzie et al., Effects of Diasprin Cross–linked Hemoglobin (DCLHb) on Cardiac Function and ECG in the Swine, Biomater. Artif. Cells Immob. Biotech., vol. 20, No. 2–4, pp. 683–687, 1992.

McKenzie et al., Effects of Diasprin Cross–linked Hemoglobin (DCLHb) on Cardiac Function and ECG in the Swine, FASEB Journal, vol. 5, No. 5, Abstract No. 1987, 1991.

McLuckie et al., Diaspirin Crosslinked Hemoglobin (DCLHb) Infusion Improves Regional Myocardial, FASEB Journal, vol. 9, No. 3, p. A9, 1995.

Messmer et al., Present State of Intentional Hemodilution, Eur. Surg. Res., vol. 18, pp. 254–263, 1986.

Nary et al., Effect of Molecular Hemoglobin on Brain Injury After Subarachnoid Hemorrhage in Rats, No Date or Publication Given.

Nary et al., Subarachnoid Hemorrhage in Rats: Effect of Molecular Hemoglobin on Hypoperfusion, Anesthesiology, vol. 83, No. 3A, p. 161, 1995, Abstract A161.

Origitano et al., Sustained Increased Cerebral Blood Flow with Prophylactic Hypertensive Hypervolemic Hemodilution ("Triple–H" Therapy) after Subarachnoid Hemorrhage, Neurosurgery, vol. 27, No. 5, pp. 729–740, 1990.

Otani et al., Reperfusion Injury Induced by Augmented Oxygen Uptake in the Initial Reperfus ion Period Possible Efficacy of Extreme Hemodilution, J. Mol. Cell. Cardiol., vol. 17, No. 5, pp. 457–466, 1985 (abstract only).

Pohl et al., Endothelium–dependent Modulation of Vascular Tone and Platelet Function, European Heart Journal, vol. 11, Supplement B, pp. 35–42, 1990.

Rebello et al., Diaspirin Crosslinked Hemoglobin Reverses the Reduction in Cerebral Blood Flow Induced by Central Endothelin (ET), The FASEB Journal, vol. 8, No. 4, Part II, Abstract No. 4802, pp. A828, 1994.

Schell et al., Hemodilution During Cerebral Ischemia in Rats: Effects of Stroma–Free Hemoglobin in Blood Flow, Anesth Analog, vol. 74, Abstract S262, 1992.

Schell et al., Hemodilution with Diaspirin Hemoglobin During Cerebral Ischemia in Rats: The Effect on Cerebral Blood Flow, No Date or Publication Given.

Siesjo, Pathophysiology and Treatment of Focal Cerebral Ischemia. Part I: Pathophysiology, Journal of Neurosuregery, vol. 77, pp. 169–184, 1992.

Siesjo, Pathophysiology and Treatment of Focal Cerebral Ischemia. Part II: Mechanisms of Damage and Treatment, Journal of Neurosuregery, vol. 77, pp. 337–354, 1992.

Sujov et al., Systemic Hemodynamics and Regional Circulatory Effects of Centrally, FASEB Journal, vol. 8, No. 4, Abstract 1926, pp. A333, 1994.

Tran et al., Effect of Diaspirin Crosslinked Hemoglobin (H) on Ventricular Fibrillation Threshold (VFT) and Acid–Based Status During Cardiopulmonary Resuscitation (CPR), No Date or Publication Given.

Wyngaarden et al., Cecil Textbook of Medicine, 19th Edition, vol. 2, Selected pp. 2162–2165, 1992.

Yellon et al., Myocardinal Protection: The Pathophysiology of Reperfusion and Reperfusion Injury, Chemical Abstracts, Abstract No. 126261t, vol. 116, No. 13, p. 640, 1992.

Zikria et al., A Biophysical Approach to Capillary Permeability, Surgery, vol. 105, No. 5, pp. 625–631, 1989.

Zikria et al., Hydroxyethyl Starch Macromolecules Reduce Myocardial Reperfusion Injury, Arch Surgery, vol. 125, pp. 930–934, 1990.

THERAPEUTIC ADMINISTRATION OF HEMOGLOBIN IN CARDIAC ARREST

BACKGROUND OF THE INVENTION

Cardiac arrest is a desperate clinical event in which the heart ceases its normal pumping action and devolves into ventricular fibrillation. Unless spontaneous circulation is restored, death from anoxia is rapid. The treatment for cardiac arrest is now standardized in the Handbook for Adult and Pediatric Providers, "Advanced Cardiac Life Support: Algorithms and Drugs",American Heart Association, reproduced from *JAMA*, 268: 2199 (1992), which sets out in detail the recommended procedures for administration of drugs and physical intervention in cardiopulmonary resuscitation (CPR).

These procedures call for opening an adequate airway to the patient, providing positive-pressure ventilation, giving chest compressions, and inducing defibrillation. These procedures are supported by administration of appropriate drugs. The Handbook referred to above lists the drugs and provides detailed instructions for their respective indications and recommended dosages. In addition there have been many experimental studies in which various drugs have been evaluated. For example, Capparelli, et al., *Crit. Care Med.*, 20: 1140 (1992) describes improved resuscitation in dogs undergoing cardiac arrest upon treatment with diltiazem. Similarly, administration of lidocaine dramatically improved arterial pressure, left ventricular pressure and carotid blood flow in the dog model during cardiopulmonary resuscitation (See Chow, et al., *J. Pharm. and Exper. Ther.*, 224: 531 (1983).

One of the consequences of cardiac arrest followed by CPR is venous acidosis. Bleske, et al., *Am. J. Emerg. Med.*, 10: 525 (1992) describes the administration of sodium bicarbonate during CPR to control acidosis. Because of the high incidence of mortality during cardiac arrest, even when the current CPR algorithms are adhered to, strategies for combination therapies are needed to improve patient survival.

SUMMARY OF THE INVENTION

The present invention provides a method of treatment for improving return of spontaneous circulation during CPR attending cardiac arrest. Return of spontaneous circulation, or alternatively termed, successful resuscitation, is defined as an organized rhythm with an unassisted systolic blood pressure of greater than 60 mm Hg for a period equal to or greater than 2 minutes.

In the present method of resuscitating a mammal undergoing cardiac arrest, stroma-free chemically crosslinked, conjugated, or polymerized hemoglobin is administered during ventricular fibrillation in a dose ranging from 50 to 2500 mg per kg of body weight, while simultaneously performing standard cardiopulmonary resuscitation (CPR) procedures, and then defibrillating electrically to effect return of spontaneous circulation. CPR includes, specifically, chest compression which is a procedure for mechanically compressing the thoracic walls to contract and expand the blood volume contained in the heart. This normal working of the heart valves prevents backflow of blood which is expelled during the compression step, thereby simulating blood circulation while the heart is unable to sustain regulated contractions on its own.

It is also desirable to reduce or eliminate acidosis occurring during CPR. Coadministration of sodium bicarbonate solutions in a dose range of 0.01 to 1.0 meq per kg of body weight per minute during CPR is efficacious for this purpose. Other drugs such as epinephrine, lidocaine or atropine may also be simultaneously administered in accordance with the Advanced Cardiac Life Support guidelines, supra.

DETAILED DESCRIPTION OF THE PREFERRED EMBODIMENT

Figure 1:
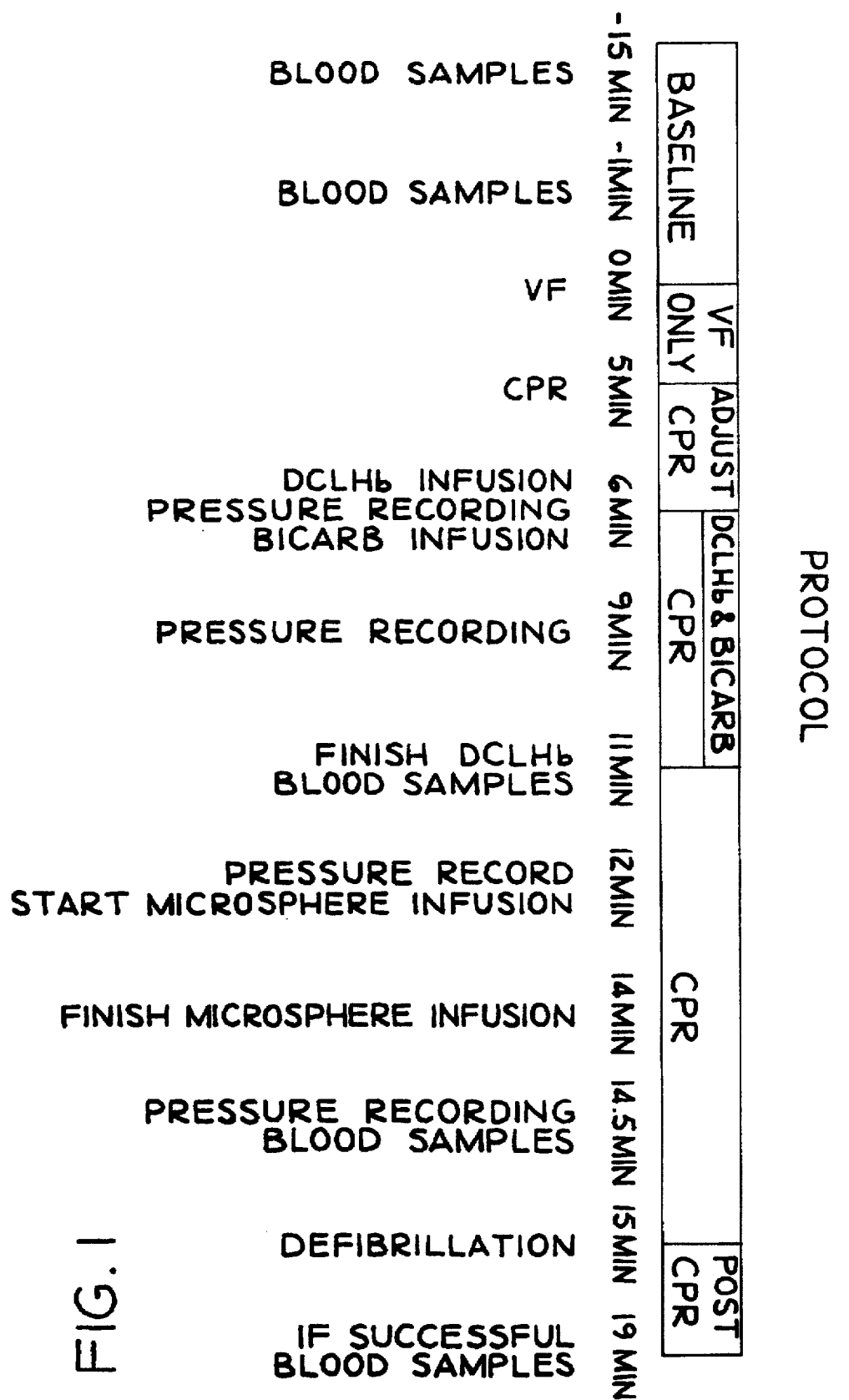
FIG. 1 is a diagram illustrating the experimental protocol set forth in the Example.

In the present method, the administration of hemoglobin by infusion (intravenous or intraarterial infusion or cannulation) is intended to augment rather than contravene the standard CPR measures established by the American Heart Association in its Advanced Cardiac Life Support Handbook, supra. The same indications prompted by clinical observation should be adhered to as are recommended in the Handbook. Infusion of hemoglobin should be instituted immediately upon determination of cardiac arrest. As a practical matter, at least several minutes may lapse before a correct diagnosis is made. Since the hemoglobin is understood to act at least in part by increasing tissue perfusion, it is important that contact between the blood-borne hemoglobin and important tissues of the heart and brain be made quickly. The other mechanical and pharmaceutical interventions of CPR are carried out simultaneously.

In resuscitation of patients undergoing cardiac arrest, there is a necessary correlation between return of spontaneous circulation and successful resuscitation, since restoration of normal pumping action must occur if the heart is to survive. Spontaneous circulation means a correction of ineffectual fibrillation to ventricular contraction effective for displacing blood contained in the heart chamber to the aorta with regular sinus rhythm. Many of the drugs used in connection with cardiac arrest have the properties of helping to establish and maintain this action, and to suppress arrhythmias. The mechanisms by which these drugs act have in some cases been at least partially elucidated. The mechanism of the present invention involving infusion of hemoglobin is unknown, but the administration of hemoglobin during CPR significantly improves return of spontaneous circulation.

The hemoglobin utilized in the present invention may be of any type which is stroma-free and modified chemically to prevent subunit dissociation and to increase the oxygen binding affinity to the range of $P_{50}$ values between about 20 and 45 mmHg. The modified hemoglobin may be a conjugated hemoglobin, crosslinked hemoglobin, or polymerized hemoglobin.

Several examples of hemoglobin modification technology have been described in the scientific literature which may be used to advantage in the practice of the present invention. For example, see the review contained in Winslow, R. M., *Hemoglobin-based Red Cell Substitutes*, The John Hopkins U. Press (1992). More specifically, the methods of making chemically modified hemoglobin are set forth hereinafter.

A conjugated hemoglobin is one to which a non-protein macromolecule is bound covalently to hemoglobin. One example is a hemoglobin chemical modified by polyalkylene glycol, which is described together with a process for its preparation in PCT application no. 91/07190 (Enzon). An example of a hemoglobin conjugated to poly(alkylene oxide) and a process for its preparation are provided in U.S. Pat. Nos. 4,301,144, 4,412,989 and 4,670,417, and in Japanese Patent Nos. 59-104323 and 61-053223 (Ajinomoto). Hemoglobin may be conjugated to inulin in a process disclosed in U.S. Pat. No. 4,377,512 (Ajinomoto). PCT application no. 91/07190, U.S. Pat. Nos. 4,301,144, 4,670, 412, 4,377,512 and Japanese Patent Nos. 59-104323 and 61-053223 are hereby incorporated by reference.

A crosslinked hemoglobin contains an intramolecular chemical link. Examples of crosslinked hemoglobins and methods for their preparation are described in U.S. Pat. Nos.

4,001,401 and 4,053,590, which disclose intramolecular crosslinking between an alpha and beta subunit of a hemoglobin tetramer utilizing compounds such as halogenated cycloalkanes, diepoxides, and diazobenzidines. In the present method, a preferred modified hemoglobin is crosslinked with bis(3,5-dibromosalicyl)fumarate to create a fumarate crosslink between the two alpha subunits. This crosslinked hemoglobin is more fully described, together with methods for its preparation, in U.S. Pat. Nos. 4,598,064, 4,600,531, RE 34,271, omitting the chromatography step. It is preferably manufactured under the conditions disclosed in U.S. Pat. No. 5,128,452 (Hai) to prevent crosslinking between β chains. U.S. Pat. Nos. 4,598,064, 4,600,531, RE 34,271 and U.S. Pat. No. 5,128,452 are hereby incorporated by reference. PCT application no. 90/13309 (Staat Der Nederlanden De Minister van Defeuric) discloses a method for crosslinking hemoglobin through a β-β linkage. The preferred diaspirin crosslinked hemoglobin will hereafter be referred to as "DCLHb".

A polymerized hemoglobin is one in which intermolecular cross-linking of hemoglobin tetramers has been used to increase the molecular weight of the modified hemoglobin. An example of a polymerized hemoglobin and a process for its preparation are described in U.S. pending application Ser. No. 08/149,679 (now abandoned), 08/173,882, 08/480,593 (now abandoned) and 08/473,459. U.S. Pat. No. 4,777,244 discloses a method for crosslinking and polymerizing with aliphatic dialdehydes. The foregoing patents are hereby incorporated by reference.

A hemoglobin that has been modified by a combination of methods is exemplified by the following. Hemoglobins modified by pyridoxal-5'-phosphate to adjust the oxygen affinity and by polyethylene glycol conjugation and processes for its preparation are described in Japanese Patent Nos. 59-089629, 59-103322 and 59-104323 Ajinomoto). U.S. Pat. No. 5,248,766 discloses a crosslinking polymerizing strategy and a process for covalently interconnecting tetrameric units with oxiranes to form polyhemoglobins with molecular weights in excess of 120,000 Daltons. The foregoing patents disclosing polymerized hemoglobins, U.S. Pat. Nos. 5,194,590, 5,248,766, Japanese Patent Nos. 59-103322, 59-089629 and 59-104323, are hereby incorporated by reference.

Hemoglobin may be modified by site-directed mutagenesis and expressed in micro-organisms or transgenic animals. Recombinant mutant and artificial hemoglobin and its production in cell cultures or fluids is described in U.S. Pat. No. 5,028,588 (Somatogen). Di-alpha and di-beta globin-like polypeptide(s) used for production of hemoglobin in bacteria and yeast are described in PCT application no. 90/13645 (Somatogen). A non-natural multimeric hemoglobin-like protein is described in PCT application no. 93/09143 (Somatogen). In general any method of crosslinking, polymerizing, encapsulating or genetically modifying, or combination thereof which yields a free tetramer having a $P_{50}$ in the operative range of 20 to 45 mmHg will have efficacy in the present method. Conditions may be adjusted for each such crosslinked tetramer or polymer derived therefrom without undue experimentation.

The dosage of hemoglobin administered in the present method may vary over a range of 50 to 2500 mg per kg of body weight. Larger doses may be indicated in situations where return to spontaneous circulation is more protracted or difficult, or where restored circulation is unstable. Dosage is also influenced by the type and dose of other drugs administered simultaneously or in sequence post-cardiac arrest. In general, repeat treatment after return of spontaneous circulation is unnecessary, unless another episode of cardiac arrest occurs.

Another benefit of hemoglobin therapy is increased perfusion to the brain. One problem in resuscitation from cardiac arrest, is the loss of blood flow to the brain resulting in ischemia and brain damage. It is possible that successful resuscitation will only result in an incurable vegetative state. The use of hemoglobin to enhance perfusion and minimize brain cell damage thus has a secondary advantage. Other advantages will be apparent from the Example which follows.

EXAMPLE

Ventricular fibrillation (VF) was induced by direct current stimulation to the right ventricle of test pigs. The pigs were paced from the right ventricular apex at a rate of 200 to 235 bpm for eight beats using a current equal to twice the pacing threshold. The intensity of the electrical stimulus was increased in 2 mA increments until VF developed. After the induction of VF, ventilation was stopped for five minutes. Then, cardiopulmonary resuscitation (CPR) was started using a pneumatic chest compression device (Thumper). The thumper was set at 80 compressions per minute with a force sufficient to achieve an aortic blood pressure of 50 to 65 mm HG. After five compressions, diastole was prolonged by 0.5 seconds and the lungs inflated to an inspiratory pressure of approximately 20 cm $H_2O$ by a synchronized pressure limited ventilator with room air. The CPR was stopped at 15 minutes and followed with external defibrillation which was attempted at 200 J. If needed, the shocks were repeated at 300 J and then at 360 J until sinus rhythm (SR) was restored. If the pigs could not achieve or maintain a blood pressure $\geq 60$ mm Hg with organized sinus rhythm, 100% oxygen was added and epinephrine, lidocaine or atropine were administered according to the American Heart Association (AHA) and Advanced Cardiac Life Support (ACLS) guidelines. Successful resuscitation was defined as return of spontaneous circulation (ROSC) post-defibrillation with a blood pressure $\geq 60$ mm Hg for at least two minutes with or without additional $O_2$ or drugs (see protocol shown in FIG. 1).

Blood samples were collected at baseline, and then at 11 minutes, and 14 minutes post-induction of ventricular fibrillation (corresponding to 6 and 9 minutes of initiation of CPR) from the femoral artery, internal jugular vein, and pulmonary artery for measurement of blood gases (238 pH blood gas analyzer, Ciba Corning, Mass.), lactate concentration (ultraviolet method, Sigma Chemical Co., St. Louis, Mo.), hemoglobin concentration (coulter counter method), and hematocrit (coulter counter method).

The colored microspheres were injected into the left ventricle at baseline and during CPR. The blood samples were collected over two minutes for the calculation of total cardiac output. Organ samples were collected at the end of the experiment for measuring of organ blood flow. Aortic, left ventricular, and pulmonary artery pressure were monitored during the study and recorded at 0, 6, 9, 12, 14 minutes of fibrillation (see protocol shown in FIG. 1).

One minute after the initiation of CPR (t=6 minutes of ventricular fibrillation), DCLHb or normal saline (control treatment) were infused over a 5 minute time interval in a random and blinded manner. The total dose of DCLHb or normal saline administered in each animal was either 5 ml/kg or 15 ml/kg. All animals also received sodium bicarbonate infusion at 0.1 meg/kg/min at the beginning of CPR to decrease development of acidosis (see protocol shown in FIG. 1).

The outcome of the treatment is shown in Table 1. Two pigs in the control group (saline treatment) compared to 6 in the DCLHb group achieved a return of spontaneous circulation (ROSC; p<0.05) at the end of 15 minutes of VF following defibrillation (see FIG. 1).

TABLE 1

| Pig # | Pressure (mm Hg) LV | A | PA | Drug | # Shock | ROSC* |
|---|---|---|---|---|---|---|
| | | | | Control | | |
| 14 | 132/0 | 97/59 | 29/9 | YES | 1 | YES |
| 20 | 66/0 | 54/10 | 33/10 | YES | 3 | YES |
| 3 | | | | YES | 3 | NO |
| 6 | | | | YES | 3 | NO |
| 8 | | | | YES | 3 | NO |
| 11 | | | | YES | 3 | NO |
| 12 | | | | YES | 3 | NO |
| 16 | | | | YES | 3 | NO |
| | | | | DCLHb | | |
| 2 | | 94/75 | | NO | 1 | YES |
| 5 | 68/4 | 74/26 | 62/12 | YES | 2 | YES |
| 13 | 88/11 | 83/59 | 15/8 | YES | 2 | YES |
| 15 | 90/4 | 80/48 | 15/5 | YES | 3 | YES |
| 17 | 92/9 | 86/71 | 37/5 | NO | 1 | YES |
| 21 | 80/1 | 74/21 | | YES | 1 | YES |
| 4 | | | | YES | 3 | NO |
| 9 | | | | YES | 3 | NO |

*p < 0.05 (control vs. DCLHb using Chi Square analysis)
Abbreviations: LV - left ventricular; PA - pulmonary artery; A - aortic.
Drug: either of epinephrine, lidocaine or atropine used during ACLS
Shock: number of DC shocks delivered to achieve defibrillation The mean blood gases obtained at arterial (from aorta), venous (from pulmonary artery), and internal jugular venous sites are summarized in Table 2. Significantly better venous pH, venous $pCO_2$ were observed in the DCLHb treatment group compared to the control group.

The mean $O_2$ content is also summarized as shown in Table 3. Significantly high venous $O_2$ content were observed in the DCLHb treatment group compared to the control group.

The mean blood pressures at different sites are summarized in Table 4. Significantly higher cerebral perfusion pressures (Cepp) were observed in the DCLHb group compared to the control group (p<0.05). Although not statistically significantly different, other mean systolic and diastolic pressures were generally higher in the DCLHb group. A decrease in coronary perfusion pressure (Copp) at 14 minutes compared to 6 minutes (beginning of CPR) were observed in 6 of 8 control animals as compared to 2 of 8 DCLHb treatment animals (p<0.05).

The total cardiac output, myocardial blood flow, and cerebral blood flow during normal sinus rhythm (baseline) and CPR in the two groups are shown in Tables 5, 6, and 7. The mean cardiac output during CPR ranged from 17–21% of baseline, whereas the mean cerebral blood flow during CPR ranged 48 to 78% of baseline, indicating a preferential shunting of flow to the brain during CPR. The mean myocardial flow during CPR ranged only 7–10% of baseline, indicating the critical nature of the myocardium during CPR. There was a trend toward higher myocardial flow during CPR in the DCLHb group, however no statistically significant difference was observed for all flow parameters between the 2 groups due to large variability observed in these measured values.

In the present study of 16 immature pigs that suffered 5 minutes of fibrillation arrest followed by 10 minutes of CPR, DCLHb treatment significantly improved resuscitation (great ROSC at the end of CPR) as compared to saline treatment. This improved resuscitation in the DCLHb group is accompanied by significantly better venous $O_2$ content and less coronary perfusion pressure deterioration.

Based upon the results obtained in the present study, DCLHb appeared to improve resuscitation post-cardiac arrest and CPR in this animal model. The beneficial effect of DCLHb may be related to improved oxygen delivery during CPR.

| | Control group | | | DCLHb group | | |
|---|---|---|---|---|---|---|
| Parameter | baseline | 11 min | 14 min | baseline | 11 min | 14 min |
| pH(A) | 7.41 ± 0.03 | 7.38 ± 0.14 | 7.36 ± 0.18 | 7.40 ± 0.03 | 7.41 ± 0.10 | 7.44 ± 0.10 |
| pH(V) | 7.37 ± 0.04 | 7.03 ± 0.31 | 7.04 ± 0.28* | 7.37 ± 0.04 | 7.28 ± 0.07 | 7.27 ± 0.07 |
| pH(IJ) | 7.37 ± 0.04 | 7.30 ± 0.18 | 7.31 ± 0.22 | 7.37 ± 0.03 | 7.29 ± 0.11 | 7.29 ± 0.10 |
| $pCO_2$ (A) | 41.13 ± 2.59 | 40.00 ± 11. | 43.25 ± 14.0 | 42.63 ± 2.67 | 37.25 ± 10.42 | 36.83 ± 12.12 |
| $pCO_2$ (V) | 49.13 ± 3.87 | 99.71 ± 44. | 92.50 ± 34.0 | 46.38 ± 3.42 | 61.86 ± 20.22 | 57.13 ± 15.83 |
| $pCO_2$ (IJ) | 48.63 ± 8.45 | 68.00 ± 24. | 71.14 ± 36.8 | 48.63 ± 6.12 | 63.00 ± 13.39 | 64.38 ± 17.08 |
| O2 sat(A) | 96.09 ± 1.93 | 88.30 ± 7.0 | 87.08 ± 9.29 | 96.49 ± 1.31 | 90.89 ± 5.15 | 90.77 ± 4.41 |
| O2 sat(V) | 77.73 ± 16.2 | 30.96 ± 14. | 31.00 ± 14.5 | 87.11 ± 3.52 | 46.40 ± 15.23 | 43.60 ± 15.82 |
| O2 sat(IJ) | 79.51 ± 13.7 | 47.17 ± 9.8 | 43.60 ± 10.1 | 86.13 ± 13.3 | 52.66 ± 21.77 | 50.60 ± 20.43 |
| $pO_2$ (A) | 90.13 ± 22.6 | 60.00 ± 14. | 62.38 ± 14.8 | 90.63 ± 16.3 | 63.00 ± 12.96 | 62.00 ± 17.99 |
| $pO_2$ (V) | 47.25 ± 11.6 | 26.14 ± 4.1 | 25.50 ± 7.12 | 55.75 ± 7.50 | 29.00 ± 6.72 | 28.00 ± 6.35 |
| $pO_2$ (IJ) | 51.38 ± 15.4 | 31.75 ± 4.7 | 30.29 ± 5.22 | 55.88 ± 16.4 | 34.13 ± 8.32 | 31.63 ± 8.35 |
| O2 content(A) | 12.80 ± 0.83 | 11.88 ± 1.9 | 12.17 ± 1.94 | 13.44 ± 0.62 | 13.74 ± 1.88 | 13.87 ± 1.91 |
| O2 content(V) | 9.98 ± 2.72 | 3.48 ± 2.50 | 3.68 ± 2.89 | 12.05 ± 0.90 | 6.99 ± 2.73 | 6.61 ± 2.79 |
| O2 content(IJ) | 10.76 ± 2.31 | 5.77 ± 2.81 | 5.27 ± 2.89 | 11.91 ± 1.85 | 7.82 ± 3.48 | 7.64 ± 3.41 |
| hemoglobin(A) | 9.78 ± 0.79 | 9.83 ± 1.03 | 10.05 ± 1.01 | 10.18 ± 0.54 | 11.11 ± 0.98 | 10.96 ± 1.02 |
| hematocrit(A) | 0.33 ± 0.02 | 0.32 ± 0.03 | 0.33 ± 0.02 | 0.32 ± 0.02 | 0.31 ± 0.03 | 0.32 ± 0.03 |
| hematocrit(V) | 0.33 ± 0.02 | 0.33 ± 0.04 | 0.32 ± 0.04 | 0.33 ± 0.03 | 0.31 ± 0.04 | 0.31 ± 0.04 |
| hematocrit(IJ) | 0.34 ± 0.03 | 0.32 ± 0.06 | 0.30 ± 0.08 | 0.32 ± 0.02 | 0.32 ± 0.04 | 0.31 ± 0.04 |

*p < 0.05 at same time points,
V - at 12 min from start of fibrillation
Abbreviations:
A - arterial sample from aorta, V - venous sample, IJ - internal jugular vein sample, $O_2$ content in ml/dl (calculated as $[pO_2 \times 0.003] \pm (1.34 \times O_2 \text{ sat} \times \text{hemoglobin})] \times 1/100$

TABLE 3

O₂ Content (ml/dl)

| | Control | | | | DCLHb | | |
|---|---|---|---|---|---|---|---|
| pig # | 0 min | 11 min | 14 min | pig # | 0 min | 11 min | 14 min |
| | | | | A | | | |
| 3 | NT | NT | NT | 2 | 13.61 | 14.18 | 15.80 |
| 6 | 12.47 | 12.83 | 13.47 | 4 | 14.55 | 15.95 | 14.20 |
| 8 | 13.20 | 9.59 | 11.33 | 5 | 13.87 | 16.25 | 16.34 |
| 11 | NT | NT | NT | 9 | 12.93 | 11.21 | 12.14 |
| 12 | 13.86 | 14.99 | 15.04 | 13 | 12.48 | 13.00 | NT |
| 14 | 11.49 | 10.30 | 9.73 | 15 | 13.40 | 13.40 | NT |
| 16 | 13.29 | 11.71 | 10.75 | 17 | 13.19 | 14.56 | 12.97 |
| 20 | 12.48 | 11.75 | 12.70 | 21 | 13.49 | 11.35 | 11.77 |
| mean | 12.80 | 11.88 | 12.17 | mean | 13.44 | 13.74 | 13.87 |
| SD | 0.83 | 1.92 | 1.94 | SD | 0.62 | 1.88 | 1.91 |
| | | | | V | | | |
| 3 | NT | NT | NT | 2 | 12.21 | 8.74 | 9.7 |
| 6 | 11.59 | 3.04 | NT | 4 | 13.77 | 6.24 | 5.64 |
| 8 | 11.3 | NT | NT | 5 | 12.83 | 11.37 | 10.74 |
| 11 | NT | NT | NT | 9 | 11.44 | 3.91 | 4.58 |
| 12 | 11.8 | 7.09 | 7.08 | 13 | 10.94 | 8.8 | 7.97 |
| 14 | 4.86 | 1.22 | 1.2 | 15 | 12.05 | 5.84 | 3.72 |
| 16 | 8.9 | 4.78 | 5.08 | 17 | 11.75 | 7.84 | 7.4 |
| 20 | 11.4 | 1.25 | 1.35 | 21 | 11.41 | 3.16 | 3.12 |
| mean | 9.98 | 3.48* | 3.68 | mean | 12.05 | 6.99 | 6.61 |
| SD | 2.72 | 2.60 | 2.89 | SD | 0.90 | 2.73 | 2.79 |
| | | | | U | | | |
| 3 | NT | NT | NT | 2 | 11.03 | 10.21 | 12.36 |
| 6 | 9.14 | 5.60 | | 4 | 14.06 | 3.98 | 5.88 |
| 8 | 12.81 | 7.46 | 7.42 | 5 | 13.78 | 10.82 | 10.59 |
| 11 | NT | NT | NT | 9 | 12.35 | 5.02 | 5.83 |
| 12 | 11.67 | 9.30 | 8.38 | 13 | 11.98 | 11.37 | 9.45 |
| 14 | 6.83 | 4.05 | 3.31 | 15 | 8.21 | 4.44 | 2.61 |
| 18 | 12.43 | 6.89 | 5.82 | 17 | 12.67 | 11.75 | 9.98 |
| 20 | 11.68 | 1.31 | 1.40 | 21 | 11.16 | 4.97 | 4.46 |
| mean | 10.76 | 5.77 | 5.27 | mean | 11.91 | 7.82 | 7.54 |
| SD | 2.31 | 2.81 | 2.89 | SD | 1.85 | 3.48 | 3.41 |

*$p < 0.05$ (two groups comparing at same time point)
NT: sample not taken (not able to calculate, see Table 2 for calculation)

TABLE 4

Mean Blood Pressures

| Parameter | Baseline | 11 Min. | 14 Min. |
|---|---|---|---|
| | Control Group | | |
| (LV)s | 115.9 ± 17.86 | 82.38 ± 19.29▽ | 74.25 ± 25.94 |
| (A)s | 96.38 ± 12.42 | 62.88 ± 13.62▽ | 55.38 ± 8.91 |
| (PA)s | 18.00 ± 11.35 | 57.50 ± 19.72▽ | 54.00 ± 22.48 |
| (LV)d | 2.63 ± 2.72 | 6.00 ± 6.05▽ | 5.25 ± 4.83 |
| (A)d | 72.00 ± 14.24 | 15.25 ± 7.17▽ | 13.00 ± 9.18 |
| (PA)d | 8.50 ± 7.37 | 12.67 ± 5.47▽ | 10.00 ± 2.77 |
| CoPP | 69.38 ± 13.31 | 9.25 ± 5.12▽ | 7.75 ± 7.63 |
| CePP | 60.00 ± 10.002 | 6.33 ± 6.62*▽ | 3.40 ± 9.37** |
| | DCLHb Group | | |
| (LV)s | 120.0 ± 17.5 | 79.75 ± 23.48▽ | 70.13 ± 25.35 |
| (A)s | 110.9 ± 16.08 | 78.14 ± 18.08▽ | 64.13 ± 20.19 |
| (PA)s | 17.43 ± 18.52 | 61.71 ± 26.23▽ | 60.86 ± 25.35 |
| (LV)d | 3.63 ± 3.66 | 7.88 ± 3.14▽ | 6.38 ± 3.38 |
| (A)d | 87.00 ± 16.24 | 23.00 ± 7.48▽ | 21.25 ± 8.10 |
| (PA)d | 8.00 ± 6.37 | 10.86 ± 5.18▽ | 14.00 ± 10.25 |
| COPP | 83.38 ± 14.74 | 14.43 ± 8.56▽ | 14.50 ± 8.54 |
| CePP | 84.86 ± 16.27 | 19.29 ± 11.25▽ | 21.29 ± 8.75 |

*$p < 0.05$
**$p < 0.001$ (group A vs. group B as same time points, two-sample t-test)
▽ at 12 min. from start of fibrillation Abbreviations: A - arterial sample from aorta; V-venous sample from pulmonary artery; (LV)s and (LV)d - left ventricular systolic and diastolic blood pressure; (A)s and (A)d - aortic systolic and diastolic blood pressure; (PA)s and (PA)d - pulmonary artery systolic and diastolic blood pressure; CoPP - coronary perfusion pressure (calculated as aortic diastolic pressure - LV diastolic pressure); CePP - cerebral perfusion pressure (calculated as aortic diastolic pressure - pulmonary artery diastolic pressure).

TABLE 5

Total Cardiac Output (L/min)

| Pig # | NSR | CPR | |
|---|---|---|---|
| | Control | | |
| 3 | 3.989 | 0.553 | 13.86% |
| 6 | NO | NO | NO |
| 8 | 2.966 | 0.363 | 12.24% |
| 11 | 3.176 | 0.837 | 26.35% |
| 12 | 2.471 | 0.342 | 13.84% |
| 14 | 3.757 | 1.045 | 27.81% |
| 16 | 2.646 | 0.648 | 24.49% |
| 20 | 2.005 | 0.583 | 29.08% |
| Mean | 3.001 | 0.624 | 21.10% |
| SD | 0.705 | 0.251 | 7.43% |
| | DCLHb | | |
| 4 | 4.452 | 0.412 | 9.25% |
| 7 | 4.811 | 1.116 | 23.20% |
| 9 | 3.832 | 0.312 | 8.14% |
| 13 | 3.119 | 0.75 | 24.05% |
| 15 | 2.478 | 0.304 | 12.27% |
| 17 | 2.393 | 0.53 | 22.15% |
| 19 | 3.381 | 0.48 | 14.20% |
| 21 | 4.273 | 0.849 | 19.87% |
| Mean | 3.592 | 0.594 | 16.64% |
| SD | 0.902 | 0.287 | 6.44% |

NSR: during normal sinus rhythm
CPR: during cardiopulmonary resuscitation
NO: flow not obtained

TABLE 6

Myocardial Blood Flow (ml/organ/min)

| Pig # | NSR | CPR | |
|---|---|---|---|
| | Control | | |
| 3 | 108.9 | 1.7 | 1.56% |
| 6 | NO | NO | NO |
| 8 | 81.3 | 3.8 | 4.67% |
| 11 | 115.9 | 13.3 | 11.48% |
| 12 | 116.1 | 1.4 | 1.21% |
| 14 | 81.4 | 14.4 | 17.57% |
| 16 | 101 | 7.6 | 7.52% |
| 20 | 74.9 | 4.5 | 6.01% |
| Mean | 97.07 | 6.66 | 7.15% |
| SD | 17.60 | 5.30 | 5.79% |
| | DCLHb | | |
| 4 | 134.6 | 3.1 | 2.30% |
| 7 | 148.5 | 18.4 | 12.39% |
| 9 | 99.6 | 1.6 | 1.61% |
| 13 | 94.2 | 14.9 | 15.82% |
| 15 | 53.3 | 1.3 | 2.44% |
| 17 | 126.1 | 21.1 | 16.73% |
| 19 | 140 | 14.1 | 10.07% |
| 21 | 188.9 | 36.6 | 19.38% |
| Mean | 123.15 | 13.89 | 19.38% |
| SD | 40.82 | 12.04 | 7.17% |

NSR: during normal sinus rhythm
CPR: during cardiopulmonary resuscitation
NO: flow not obtained

TABLE 7

| Cerebral Blood Flow (ml/organ/min) | | | |
|---|---|---|---|
| Pig # | NSR | CPR | |
| Control | | | |
| 3 | 34.3 | 17.6 | 51.31% |
| 6 | NO | NO | NO |
| 8 | 18.4 | 6.3 | 34.24% |
| 11 | 19.5 | 2D.7 | 106.15% |
| 12 | 20.7 | 16.3 | 78.74% |
| 14 | 25.3 | 29.4 | 116.21% |
| 16 | 25.5 | 15.1 | 59.22% |
| 20 | 15.2 | 14.S | 97.37% |
| Mean | 22.70 | 17.17 | 77.61% |
| SD | 6.30 | 6.96 | 30.57% |
| DCLHb | | | |
| 4 | 34.7 | 11 | 31.70% |
| 7 | 25.5 | 12.9 | 50.59% |
| 9 | 26.7 | 8.4 | 31.46 |
| 13 | 27.5 | 26.1 | 94.91% |
| 15 | 23.5 | 3.5 | 14.89% |
| 17 | 34.6 | 25.7 | 74.28% |
| 19 | 23.1 | 12.7 | 54.98% |
| 21 | 36.2 | 12.5 | 34.53% |
| Mean | 28.98 | 14.10 | 48.42% |
| SD | 5.35 | 7.92 | 26.08% |

What is claimed is:

1. A method for resuscitation of a patient undergoing cardiac arrest comprising:

systemically administering stroma-free hemoglobin to a patient experiencing ventricular fibrillation during cardiac pulmonary resuscitation of the patient; and defibrillating to effect return of spontaneous circulation in the patient.

2. A method of claim 1 wherein the cardiac pulmonary resuscitation includes mechanically compressing thoracic walls to alternatively contract and expand blood volume contained in a heart, thereby simulating pumping action of the heart.

3. A method of claim 1 wherein the stroma-free hemoglobin is administered in a dose ranging from 50 to 2,500 mg/kg of body weight.

4. A method of claim 1 wherein the stroma-free hemoglobin has a $P_{50}$ of from about 20 to about 45 mm Hg.

5. A method of claim 1 wherein the stroma-free hemoglobin is chemically modified hemoglobin.

6. A method of claim 5 wherein the chemically-modified hemoglobin is crosslinked, conjugated or polymerized hemoglobin.

7. A method of claim 6 wherein the chemically-modified hemoglobin is diaspirin crosslinked hemoglobin.

8. A method of claim 1 wherein sodium bicarbonate is coadministered with the hemoglobin to prevent the onset of acidosis during cardiac pulmonary resuscitation.

9. A method of claim 8 wherein from 0.01 to 1.0 meq/kg of body weight of sodium bicarbonate is administered per minute.

10. A method of claim 1 wherein epinephrine, lidocaine or atropine is coadministered with the hemoglobin.

11. A method of claim 1 wherein the patient is a human.

* * * * *